United States Patent [19]

Schmidt et al.

[11] 4,440,745
[45] Apr. 3, 1984

[54] ABRASIVE COMPOSITIONS

[75] Inventors: Helmut Schmidt, Höchberg; Alfred Kaiser, Kist, both of Fed. Rep. of Germany

[73] Assignee: Fraunhofer-Gesellschaft zur Förderung der angewandten Forschung e.V., Munich, Fed. Rep. of Germany

[21] Appl. No.: 332,100

[22] Filed: Dec. 17, 1981

[30] Foreign Application Priority Data

Dec. 22, 1980 [DE] Fed. Rep. of Germany ....... 3048369

[51] Int. Cl.³ .................... A61K 31/74; A61K 31/695
[52] U.S. Cl. ........................................ 424/78; 51/308; 252/174.15; 424/184
[58] Field of Search ................... 424/78, 184; 528/39; 252/174.15; 51/308

[56] References Cited

U.S. PATENT DOCUMENTS

| | | | |
|---|---|---|---|
| 2,446,135 | 7/1948 | Hyde | 528/39 |
| 2,857,356 | 10/1958 | Goodwin | 528/39 X |
| 3,953,591 | 4/1976 | Snyder | 424/80 |
| 4,238,590 | 12/1980 | Scholze et al. | 528/5 |
| 4,311,695 | 1/1982 | Starch | 424/184 |
| 4,374,696 | 2/1983 | Schmidt et al. | 156/329 |
| 4,374,933 | 2/1983 | Scholze et al. | 521/64 |

OTHER PUBLICATIONS

"The Condensed Chemical Dictionary", p. 699.
Dr. Otto-Albrecht Neumuller, "Rompps Chemie-Lexikon", p. 2194.
"Van Nostrand's Scientific Encyclopedia" p. 814.

Primary Examiner—Leonard Schenkman
Attorney, Agent, or Firm—Birch, Stewart, Kolasch & Birch

[57] ABSTRACT

Abrasive compositions comprising a porous, organo-modified silicic acid heteropolycondensate as abrasive and one or more conventional components selected from the group of carriers, adjuvants and active substances such as pharmaceuticals, disinfectants, insecticides, bactericides, etc. The compositions are useful in medical and cosmetic applications, such as in the treatment of acne or as a tooth paste, and also in various technical and industrial fields, e.g., as a polishing or cleansing material.

8 Claims, No Drawings

ABRASIVE COMPOSITIONS

BACKGROUND AND SUMMARY OF THE INVENTION

The invention relates to abrasive compositions suitable for medical and cosmetic purposes such as the treatment of acne, and for technical applications, e.g. as polishing materials for delicate surfaces.

Abrasive compositions conventionally comprise an abrasive or scouring component that may be combined with a variety of carriers, adjuvants and active substances, depending on the intended use. Some fields of application call for abrasive compositions which are adjustable as to their abrasive or scouring action. Of particular interest are compositions showing a gradual, controlled decline of abrasive or scouring action during use.

The above problem is encountered, for instance, in cosmetic preparations for the treatment of acne. If conventional abrasives such as sand, silicates, silica gels or aluminum oxide are added to such preparations, the constant scouring action, particularly with excessive use of the preparation, would cause irritations and damage to the skin. For this reason, cosmetic preparations usually comprise sodium tetraborate (borax) as an abrasive in a conventional soap base. Sodium tetraborate has the advantage of a hardness suitable to the intended purpose while its scouring action gradually diminishes through the abrasion effected, thus preventing any damage to the skin. Recently, however, it has been discovered that boron compounds may be detrimental to the health of the user and as a result, e.g. boric ointments have practically all been taken from the market.

Also known is the use of sodium chloride as an abrasive in cosmetic preparations of the above described type. These abrasives do, however, cause skin irritations, and painful smarting of the skin, particularly with minor injuries, is frequently observed.

Surprisingly, it has now been found that porous organo-modified silicic acid heteropolycondensates provide excellent abrasives, as their abrasive or scouring action, both absolute and as a function of time, is adjustable in a defined manner.

Because of these characteristics, the abrasives of the invention are suitable not only for medical or cosmetic preparations such as acne treating compositions or tooth pastes, but for technical and industrial applications as well, e.g. in cleansing and polishing materials for paint coatings, enamels or other delicate surfaces.

DETAILED DESCRIPTION OF THE INVENTION

The porous silicic acid heteropolycondensates used as abrasives in the compositions of the invention are prepared by hydrolytic polycondensation of one or more silanes or polysiloxanes with at least one silane or polysiloxane having one or more organic radicals bound to silicon.

Preferred silicic acid heteropolycondensates are copolycondensates of completely hydrolyzable silanes such as tetraalkoxysilanes or polyalkoxysiloxanes, with organo-silanes. The proportion of completely hydrolyzable silanes is adjusted to a value sufficiently high to provide a porous product.

According to a particularly preferred embodiment, the abrasives employed are silicic acid heteropolycondensates that have been prepared by hydrolysis and polycondensation of:

(a) at least one silicon-functional silane of the general formula (I):

$$SiX_4 \qquad (I),$$

wherein X is hydrogen, halogen, alkoxy, acyloxy or an $-NR_2$ group, in which R is hydrogen and/or alkyl, with the proviso that not all of X are hydrogen;

(b) at least one organo-silane of the general formula (II):

$$SiR'_a X_{(4-a)} \qquad (II),$$

wherein X is as defined above; R' is alkyl, alkenyl, aryl, aralkyl or alkylaryl; and a is an integer of 1, 2 or 3;

(c) optionally at least one organo-functional silane of the general formula (III):

$$SiR'_b X_c (R''Y)_{(4-b-c)} \qquad (III),$$

wherein R' and X are as defined above; R'' is straight-chain or branched alkylene, optionally interrupted by oxygen or sulfur atoms or -NH- groups; phenylene, alkylphenylene or alkylenephenylene; Y is halogen, unsubstituted or substituted amino, unsubstituted or substituted anilino, or an aldehyde, keto, carboxy, hydroxy, mercapto, cyano, hydroxyphenyl, diazo, carboxylic acid alkyl ester, sulfonic acid ($SO_3H$), or phosphoric acid ($PO_3H_2$) group; b is 0 or an integer of 1 or 2; c is an integer of 1, 2 or 3; and sum of b+c is an integer of 1, 2 or 3; and/or (d) optionally at least one compound selected from the group consisting of substantially involatile oxides of elements selected from the group consisting of the main group Ia to Va and the side groups IVb or Vb of the Periodic Table, which are soluble in the reaction medium, and compounds of these elements which are capable of forming a substantially involatile oxide soluble in the reaction medium, in the presence of at least the amount of water stoichiometrically required for hydrolysis and, optionally, in the presence of a condensation catalyst and/or an organic solvent, followed by separation of any organic solvent present, and drying and comminuting of the silicic acid heteropolycondensate obtained.

Based upon the oxide units, the silicic acid heteropolycondensate thus prepared comprises from 35 to 90% by weight of component (a), from 10 to 50% by weight of component (b), from 0 to 15% by weight of component (c), and from 0 to 40% by weight of component (d).

The above and similar silicic acid heteropolycondensates as well as methods of preparing the same are described e.g. in U.S. Pat. No. 4,238,590 and German OS 2,925,969. Preferred compositions of the products and specific examples of components (a) to (d) may be taken from the above patents, the disclosure of which is hereby expressly incorporated herein by reference.

Obviously, for medical and cosmetic applications, the components (a) to (d) and specifically the oxide component (d) must be non-toxic and pharmaceutically or cosmetically acceptable. Particularly suitable oxide components (d) of that type are oxides as well as oxide-forming compounds of Al, Ca, Mg, Ti, Zr, Zn and Si.

After condensation, silicic acid heteropolycondensates thus obtained may be washed, dried, comminuted and fractionated.

The abrasives of the invention usually have a particle size of e.g. from about 0.01 to 1 mm, preferably from 0.1 to 0.5 mm, and particularly from 0.2 to 0.4 mm. For specific applications, particle sizes above or below these limits may also be employed.

The hardness of the abrasives varies between 1 and 5 on the Mohs scale. Hardness may be adjusted e.g. by the composition of the silicic acid heteropolycondensate and the rate of condensation. High proportions of components (a) and/or (d) result in harder products; in a similar manner, low condensation rates lead to hard, coarsely grained compact products, while high condensation rates provide soft, finely grained voluminous powders.

The abrasive compositions of the invention comprise the abrasive in combination with conventional carriers, adjuvants and/or active ingredients. The abrasive content may vary between 1 and 99% based on the total weight of the composition; it is usually from 2 to 50%, preferably from 3 to 30%, and particularly from 5 to 15% by weight thereof.

The compositions may be formulated as aqueous or oily suspensions, shaking mixtures, emulsified ointments, non-aqueous ointments, pastes, creams, gels, powders or foams. They may be applied to or incorporated into paper or non-woven fabrics made of cellulose, textiles, or synthetic or glass fibers. Another possible mode of application is to blast the abrasive with a gas stream onto the substrate to be treated.

The carriers used in the above and other embodiments may be solid, semi-solid, liquid or gaseous. Illustrative of such carriers are water, aqueous solutions, organic solvents such as alcohols, glycols, polyglycol ethers, ketones, aliphatic and aromatic hydrocarbons or hydrocarbon halides, petroleum fractions, paraffin oils, as well as animal or vegetable oils or fats; clays, kaolin, bentonite, talcum, diatomaceous earth, titania, clacium carbonate or starch; air, inert gases, carbon dioxide or freons.

For medical and cosmetic applications, the preferred carrier is an ointment base such as W/O or O/W emulsions; paraffinic hydrocarbons, e.g. petroleum jelly or paraffin; silicone bases or fatty bases. Suitable carriers also include active washing substances such as nonionic, cationic, amphoteric or preferably anionic surfactants, conventional soaps or syndets. Specifically suitable surfactants are such commercial products as TEXAPON ® (Henkel), HOSTAPON ® (Hoechst), LAMEPON ® (Chemische Fabrik Grünau GmbH), and LATHANOL ® (Allied Chemical Corporation).

Depending on the intended use, the compositions of the invention may contain a variety of adjuvants such as buffers; binders, e.g. cellulose derivatives, starch, gelatin gum arabic or tragacanth; anionic, cationic, nonionic or amphoteric polymers; thickeners such as cellulose derivatives; fillers or extenders such as silica gels, silictes, carbonates, phosphates or carbohydrates; skin softeners; emulsifiers such as the above mentioned surfactants, alkali phosphates or polyphosphates; dyeing agents such as organic dyes or organic or inorganic pigments; silicone oils; bleaching agents; lubricants such as metal soaps; perfumes; deodorants; flavor-improving agents; conventional abrasives and/or natural or synthetic waxes such as beeswax, Carnauba wax or lignite wax.

If desired, active ingredients may be added to the compositions, e.g. pharmaceuticals, disinfectants, preservatives, insecticides, bactericides or fungicides, antioxidants or corrosion inhibitors, all of which are well known in the art.

The abrasive compositions of the invention are employed in a conventional manner in the respective fields of application. In the medical and cosmetic fields, they serve as e.g. acne treating agents or tooth pastes, and in the technical field, they are useful as cleansing, polishing or scouring agents and as cleansers for enamels and other delicate surfaces.

The invention is illustrated hereinbelow by means of acne-treating agents. Such agents comprise the abrasive of the invention in a base of active washing substances. They may also contain e.g. reducing substances such as sulfur or resorcinol; astringents such as zinc oxide; disinfectants such as antibiotics or hexachlorophene; antiinflammatory agents such as corticosteroids; agents to reduce swelling and itching such as sulfurized shale oils, tars, camphor or phenol; or keratolytic agents such as salicylic acid.

The following non-limiting examples are given by way of illustration only. In the examples, all percentages are by weight, unless otherwise indicated.

EXAMPLE 1

95.6 ml of tetramethoxysilane $Si(OCH_3)_4$ and 26.2 ml of dimethyldiethoxysilane $(CH_3)_2Si(OC_2H_5)_2$ are dissolved in 122 ml of methanol and admixed with 52 ml of 1N $NH_3$ under stirring at room temperature. After solidification, the reaction mixture is washed with hot distilled water until the wash-water no longer shows an alkaline reaction. The condensate is dried at 110° C. and subsequently comminuted and fractionated.

The fraction having a particle size of from 0.2 to 0.4 mm is incorporated into LAMEPON S ® (proteinfatty acid condensate; aqueous solution having an active content of 32%; Chemische Fabrik Grünau GmbH in an amount of 15% to provide an ointment.

EXAMPLE 2

86.1 ml of tetramethoxysilane $Si(OCH_3)_4$ and 35.7 ml of dimethyldiethoxysilane $(CH_3)_2Si(OC_2H_5)_2$ are dissolved in 200 ml of methanol and subsequently mixed with 100 ml of 12N HCl. After brief stirring, the mixture is allowed to stand at room temperature. The solidified product is repeatedly boiled with distilled water and filtered until the filtrate shows a neutral pH. After drying at 100° C., the product is comminuted and fractionated.

The fraction having a particle size of from 0.1 to 0.3 mm is incorporated into LATHANOL ® (sodium laurylsulfoacetate; Allied Chemical Corporation) in an amount of 10% to provide an ointment.

EXAMPLE 3

A syndet soap paste is prepared from the following ingredients:

| | |
|---|---|
| silicic acid heteropolycondensate | 15% |
| IRGASAN DP 300 ® (bactericide; Ciba Geigy) | 0.1% |
| ARLACEL 165 ® (emulsifier; Atlas) | 4% |
| TEXAPON N 25 ® (surfactant; Henkel) | 6% |
| LAMEPON S ® (protein-fatty acid condensate; Chem. Fabrik Grunau GmbH) | 6% |
| LATHANOL ® powder (sodium laurylsulfoacetate; Allied Chemical Corporation) | 6% |

| HOSTAPON CT ® paste (anionic surfactant; Hoechst) | 40% |
| AEROSIL ® (silica; Degussa) | 1% |
| perfumes, dyes | ad libitum |
| aqua dist. | ad 100% |

EXAMPLE 4

A soap is prepared from 15% of silicic acid heteropolycondensate and a conventional soap base (ad 100%).

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A skin treatment composition adapted for application to the human skin comprising an effective amount of a porous, organo-modified silicic acid heteropolycondensate, said heteropolycondensate being prepared by hydrolytic polycondensation of:
   (a) from 35 to 90% by weight of at least one silicon-functional silane of the formula (I):

$$SiX_4 \qquad (I),$$

wherein X is hydrogen, halogen, alkoxy, acyloxy or an —NR$_2$ group, in which R is hydrogen and/or alkyl, with the proviso that not all of X are hydrogen;
   (b) from 10 to 50% by weight of at least one organosilane of the formula (II):

$$SiR'_a X_{(4-a)} \qquad (II),$$

wherein X is as defined above, R' is alkyl, alkenyl, aryl, aralkyl or alkylaryl; and a is an integer of 1, 2 or 3;
   (c) optionally from 0 to 15% by weight of at least one organo-functional silane of the formula (III):

$$SiR'_b X_c (R''Y)_{(4-b-c)} \qquad (III),$$

wherein R' and X are as defined above; R'' is a straight-chain or branched alkylene, optionally interrupted by oxygen or sulfur atoms or —NH— groups; phenylene, alkylphenylene or alkylenephenylene; Y is halogen, unsubstituted or substituted amino, unsubstituted or substituted anilino, or an aldehyde, keto, carboxy, hydroxy, mercapto, cyano, hydroxyphenyl, diazo, carboxylic acid alkyl ester, sulfonic acid (SO$_3$H) or phosphoric acid (PO$_3$H$_2$) group; b is 0 or an integer of 1 or 2; c is an integer of 1, 2 or 3; and the sum of b+c is an integer of 1; 2 or 3; and/or
   (d) optionally from 0 to 40% by weight of at least one compound selected from the group consisting of substantially involatile oxides of elements selected from the group consisting of the main group Ia to Va and the side group IVb or Vb of the Periodic Table, which are soluble in the reaction medium, and compounds of these elements which are capable of forming a substantially involatile oxide soluble in the reaction medium, in the presence of at least the amount of water stoichiomatrically required for hydrolysis and optionally in the presence of a condensation catalyst and/or an organic solvent, followed by removing any solvent present and drying and comminuting the silicic acid heteropolycondensate obtained, and
   at least one topically acceptable carrier or adjuvant selected from the group consisting of surfactants, soaps and syndets.

2. The composition of claim 1, further including at least one active substance selected from the group consisting of pharmaceuticals effective against acne and bactericides.

3. The composition of claim 1, wherein said silicic acid heteropolycondensate has a particle size of from about 0.01 to 1 mm.

4. A skin treatment composition adapted for application to the human skin comprising an effective amount of a porous, organo-modified silicic acid heterpolycondensate as an abrasive, said heterpolycondensate being prepared by hydrolytic polycondensation of:

(a) from 35 to 90% by weight of at least one silicon-functional silane of the formula (I):

$$SiX_4 \qquad (I),$$

wherein X is hydrogen, halogen, alkoxy, acyloxy or an —NR$_2$ group, in which R is hydrogen and/or alkyl, with the proviso that not all of X are hydrogen;
   (b) from 10 to 50% by weight of at least one organosilane of the formula (II):

$$SiR'_a X_{(4-a)} \qquad (II),$$

wherein X is as defined above; R' is alkyl, alkenyl, aryl, aralkyl or alkylaryl; and a is an integer of 1, 2 or 3;
   (c) optionally from 0 to 15% by weight of at least one organo-functional silane of the formula (III):

$$SiR'_b X_c (R''Y)_{(4-b-c)} \qquad (III),$$

wherein R' and X are as defined above; R'' is straight-chain or branched alkylene, optionally interrupted by oxygen or sulfur atoms or —NH— groups; phenylene, alkylphenylene or alkylenephenylene; Y is halogen, unsubstituted or substituted amino, unsubstituted or substituted anilino, or an aldehyde, keto, carboxy, hydroxy, mercapto, cyano, hydroxyphenyl, diazo, carboxylic acid alkyl ester, sulfonic acid (SO$_3$H) or phosphoric acid (PO$_3$H$_2$) group; b is 0 or an integer of 1 or 2; c is an integer of 1, 2 or 3; and/or
   (d) optionally from 0 to 40% by weight of at least one compound selected from the group consisting of substantially involatile oxides of elements selected from the group consisting of the main group Ia to Va and the side groups IVb or Vb of the Periodic Table, which are soluble in the reaction medium, and compounds of these elements which are capable of forming a substantially involatile oxide soluble in the reaction medium, in the presence of at least the amount of water stoichiometrically required for hydrolysis and optionally in the presence of a condenstion catalyst and/or an organic solvent, followed by removing any solvent present and drying and comminuting the silicic acid heteropolycondensate obtained, and at least one topically acceptable carrier or adjuvant selected from the group consisting of ointments, paraffinic hydrocarbons, silicone bases, and fatty bases.

5. The composition of claim 4, further including at least one active substance selected from the group consisting of pharmaceuticals effective against acne and bactericides.

6. The composition of claim 4, wherein said silicic acid heteropolycondensate has a particle size of from about 0.01 to 1 mm.

7. A method for treating acne comprising applying to the human skin an effective acne treatment amount of a composition comprising a porous, organo-modified silicic acid heteropolycondensate as an abrasive, said heteropolycondensate being prepared by hydrolytic polycondensation of:

(a) from 35 to 90% by weight of at least one silicon-functional silane of the formula (I):

$$SiR_4 \qquad (I),$$

wherein X is hydrogen, halogen, alkoxy, acyloxy or an —$NR_2$ group, in which R is hydrogen and/or alkyl, with the proviso that not all of X are hydrogen;

(b) from 10 to 50% by weight of at least one organosilane of the formula (II):

$$SiR'_a X_{(4-a)} \qquad (II),$$

wherein X is as defined above; R' is alkyl, alkenyl, aryl, aralkyl or alkylaryl; and a is an integer of 1, 2 or 3;

(c) optionally from 0 to 15% by weight of at least one organo-functional silane of the formula (III):

$$SiR'_b X_c (R''Y)_{(4-b-c)} \qquad (III),$$

wherein R' and X are as defined above; R'' is straight-chain or branched alkylene, optionally interrupted by oxygen or sulfur atoms or —NH— groups; phenylene, alkylphenylene or alkylenephenylene; Y is halogen, unsubstituted or substituted amino, unsubstituted or substituted anilino, or an aldehyde, keto, carboxy, hydroxy, mercapto, cyano, hydroxyphenyl, diazo, carboxylic acid alkyl ester, sulfonic acid ($SO_3H$) or phosphoric acid ($PO_3H_2$) group; b is 0 or an integer of 1 or 2; c is an integer of 1, 2 or 3; and/or (d) optionally from 0 to 40% by weight of at least one compound selected from the group consisting of substantially involatile oxides of elements selected from the group consisting of the main group I$a$ to V$a$ and the side group IV$b$ or V$b$ of the Periodic Table, which are soluble in the reaction medium, and compounds of these elements which are capable of forming a substantially involatile oxide soluble in the reaction medium, in the presence of at least the amount of water stoichiometrically required for hydrolysis and optionally in the presence of a condensation catalyst and/or an organic solvent, followed by removing any solvent present and drying and comminuting the silicic acid heteropolycondensate obtained, and at least one topically acceptable carrier of adjuvant.

8. A method for clensing, scouring or polishing delicate surfaces comprising applying to a delicate surface an effective amount of a composition comprising a porous, organo-modified silicic acid heteropolycondensate as an abrasive, said heteropolycondensate being prepared by hydrolytic polycondensation of:

(a) from 35 to 90% by weight of at least one silicon-functional silane of the formula (I):

$$SiX_4 \qquad (I),$$

wherein X is hydrogen, halogen, alkoxy, acyloxy or an —$NR_2$ group, in which R is hydrogen and/or alkyl, with the proviso that not all of X are hydrogen;

(b) from 10 to 50% by weight of at least one organosilane of the formula (II):

$$SiR'_a X_{(4-a)} \qquad (II),$$

wherein X is as defined above; R' is alkyl, alkenyl, aryl, aralkyl or alkylaryl; and a is an integer of 1, 2 or 3;

(c) optionally from 0 to 15% by weight of at least one organo-functional silane of the formula (III):

$$SiR'_b X_c R''Y_{(4-b-c)} \qquad (III),$$

wherein R' and X are as defined above; R'' is straight-chain or branched alkylene, optionally interrupted by oxygen or sulfur atoms or —NH— groups; phenylene, alkylphenylene or alkylenephenylene; Y is halogen, unsubstituted or substituted amino unsubstituted or substituted anilino, or an aldehyde, keto, carboxy, hydroxy, mercapto, cyano, hydroxyphenyl, diazo, carboxylic acid alkyl ester, sulfonic acid ($SO_3H$) or phosphoric acid ($PO_3H_2$) group; b is 0 or an integer of 1 or 2; c is an integer of 1, 2 or 3; and the sum of b+c is an integer of 1, 2 or 3; and/or (d) optionally from 0 to 40% by weight of at least one compound selected from the group consisting of substantially involatile oxides of elements selected from the group consisting of the main groups I$a$ to V$a$ and the side group IV$b$ or V$b$ of the Periodic Table, which are soluble in the reaction medium, and compounds of these elements which are capable of forming a substantially involatile oxide soluble in the reaction medium, in the presence of at least the amount of water stoichio-metrically required for hydrolysis and optionally in the presence of a condensation catalyst and/or an organic solvent, followed by removing any solvent present and drying and comminuting the silicic acid heteropolycondensate obtained, and at least one carrier.

* * * * *